(12) United States Patent
Pelta

(10) Patent No.: US 6,683,190 B1
(45) Date of Patent: Jan. 27, 2004

(54) METHOD FOR PREPARING CHIRAL AMINO ACIDS

(75) Inventor: Isabelle Pelta, Chassieu (FR)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 09/869,939

(22) PCT Filed: Jan. 7, 2000

(86) PCT No.: PCT/FR00/00020
§ 371 (c)(1), (2), (4) Date: Oct. 9, 2001

(87) PCT Pub. No.: WO00/40545
PCT Pub. Date: Jul. 13, 2000

(30) Foreign Application Priority Data

Jan. 7, 1999 (FR) .............................. 99 00202

(51) Int. Cl.$^7$ ............................ C07D 233/84
(52) U.S. Cl. ................ 548/315.1; 548/317.1; 548/320.5; 548/321.1; 548/499
(58) Field of Search ........... 548/315.1, 317.1, 548/320.5, 321.1, 499

(56) References Cited

U.S. PATENT DOCUMENTS

| | | | | |
|---|---|---|---|---|
| 2,557,920 A | * | 6/1951 | White et al. ................ | 548/499 |
| 3,790,599 A | * | 2/1974 | Zundel et al. ............... | 548/499 |
| 5,108,914 A | * | 4/1992 | Wagner et al. ............... | 435/106 |
| 5,326,878 A | * | 7/1994 | Depernet et al. ......... | 548/315.1 |

FOREIGN PATENT DOCUMENTS

| | | |
|---|---|---|
| EP | 0629616 | 12/1994 |
| FR | 2499560 | 8/1982 |
| WO | 9803490 | 1/1998 |

OTHER PUBLICATIONS

Puri et al. "The synthesis and reactivity of new . . ." CA 123:228745 (1995).*
Wang et al. "The simultaneous in situ . . ." CA 132:22577 (1999).*
Roggenbuck et al. "One–pot synthesis . . ." CA 132:35584 (1999).*
Periasamy et al. "A new convenient method . . ." CA 131"299276 (1999).*
Kato et al. "Practical synthesis of novel . . ." CA 134:162959 (2001).*
Patent Abstracts of Japan JP 62 103049—May 13 1987.
Patent Abstracts of Japan JP 60 224661—Nov. 9, 1985.

* cited by examiner

Primary Examiner—Ceila Chang
(74) Attorney, Agent, or Firm—Ostrolenk, Faber, Gerb & Soffen, LLP

(57) ABSTRACT

The invention concerns a novel method for preparing chiral amino acids of formula (I) characterised in that it consists in contracting a racemic hydantoin of formula (II) with an enantiomeric splitting agent.

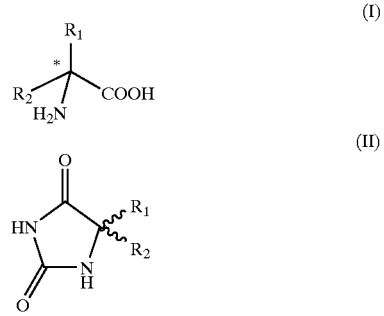

16 Claims, No Drawings

METHOD FOR PREPARING CHIRAL AMINO ACIDS

FIELD OF THE INVENTION

The present invention relates to a novel process for preparing chiral amino acids from racemic hydantoins and to the use of the said chiral amino acids as synthesis intermediates of chiral organic compounds.

PRIOR ART

Numerous processes for preparing chiral amino acids exist in the literature, based principally on processes of resolving racemic mixtures by liquid chromatography, resolution by means of alkaloids or by an enzymatic process, as for example in the as yet unpublished French patent application No. 98 06339.

These various processes of resolution present the disadvantages of being processes which are difficult to implement industrially and are of relatively high cost. In effect, the methods used are expensive.

The industrial processes—by industrial processes are meant any preparation processes other than laboratory preparations—for preparing chiral amino acids therefore necessitate enantioselective syntheses, i.e. syntheses which lead only to the single desired enantiomer and do so with a high enantiomeric purity.

Processes for preparing amino acids from hydantoins are known, for example, from the patents JP 60224661 and JP 62103049. However, these processes lead to racemic amino acids.

In contrast, the patent EP-A-739978 presents a process for preparing optically pure amino acids from racemic hydantoins.

This type of process has the drawback of employing an enzymatic reaction and of comprising a plurality of steps. This has a direct consequence on the complexity of the industrial process, on the yields of product obtained and on the production costs.

It is an object of the present invention to provide a process for preparing chiral amino acids from racemic hydantoins which does not entail the abovementioned drawbacks.

It is an object of the present invention to provide a process for preparing substantially enantiomerically pure amino acids from racemic hydantoins.

It is another object of the present invention to provide a process for preparing substantially enantiomerically pure amino acids from racemic hvdantoins which comprises only a single step (one-pot reaction), without isolation of the chiral hydantoin intermediate.

It is another object of the present invention to provide a process for preparing substantially enantlomerically pure amino acids from racemic hydantoins with a high yield.

It is an additional object of the present invention to provide a process for preparing substantially enantiomerically pure amino acids from racemic hydantoins which is easy to implement industrially and is of low cost.

It has now been found that all of these aims may be achieved in whole or in part by virtue of the process of the invention, whose description is presented below.

BRIEF DESCRIPTION OF THE INVENTION

The present invention consists in a novel process for preparing chiral amino acids of formula (I):

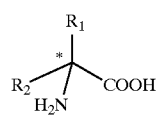

characterized in that a racemic hydantoin of formula (II):

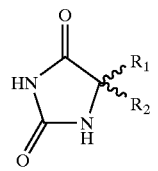

is contacted with an enantiomeric resolving agent, where, in the compounds of formulae (I) and (II):

$R_1$ and $R_2$ are different and are selected from:
  an alkyl or haloalkyl radical containing from 1 to 6 carbon atoms in a linear or branched chain;
  an alkoxyalkyl, alkylthioalkyl, alkylsulphonylalkyl, monoalkylaminoalkyl, alkenyl or alkynyl radical containing from 2 to 6 carbon atoms in a linear or branched chain;
  a dialkylaminoalkyl or cycloalkyl radical containing from 3 to 7 carbon atoms in a linear or branched chain;
  an aryl radical, i.e. phenyl, naphthyl, thienyl, furyl, pyridyl, benzothienyl, benzofuryl, qulnolinyl, isoquinolinyl or methylenedioxyphenyl radical, optionally substituted by from 1 to 3 groups selected from $R_6$; and
  an arylalkyl, aryloxyalkyl, arylthioalkyl or aryisulphonylalkyl radical, the terms aryl and alkyl having the definitions given above;
or else
  $R_2$ and $R_2$, together with the carbon atom to which they are attached on the ring, may form a carbocycle or a heterocycle containing from 5 to 7 atoms, it being possible for these rings to be fused with a phenyl optionally substituted by from 1 to 3 groups selected from $R_6$;

$R_6$ represents a radical selected from:
  a halogen atom;
  an alkyl, haloalkyl, alkoxy, haloalkoxy, alkylthio, haloalkylthio or alkylsulphonyl radical containing from 1 to 6 carbon atoms;
  a cycloalkyl, halocycloalkyl, alkenyloxy, alkynyloxy, alkenylthio, alkynylthio radical containing from 3 to 6 carbon atoms;
  the nitro or cyano group;
  an amino radical optionally mono- or disubstituted by an alkyl or acyl radical containing from 1 to 6 carbon atoms or alkoxycarbonyl radical containing from 2 to 6 carbon atoms; and
  a phenyl, phenoxy or pyridyloxy radical, these radicals being optionally substituted by from 1 to 3 identical or different groups selected from $R_7$; and $R_7$ represents a radical selected from:
  a halogen atom selected from fluorine, chlorine, bromine and iodine;
  a linear or branched alkyl radical containing from 1 to 6 carbon atoms;
  a linear or branched alkoxy or alkylthio radical containing from 1 to 6 carbon atoms;

a linear or branched haloalkoxy or haloalkylthio adical containing from 1 to 6 carbon atoms;
a nitrile radical; and
a nitro radical.

The chiral amino acids thus obtained may serve as synthesis intermediates in the preparation of chiral active substances which are useful particularly in therapy or in agriculture. By way of example, these chiral amino acids may be used as intermediates in the preparation of certain fungicidal 2-imidazolin-5-ones and 2-imidazoline-5-thiones described in the patent EP-A-0 629 616.

DETAILED DESCRIPTION OF THE INVENTION

The present invention concerns a novel process for preparing chiral amino acids of formula (I):

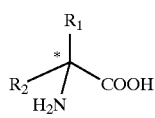

in which:
$R_1$ and $R_2$ are different and are selected from:
an alkyl or haloalkyl radical containing from 1 to 6 carbon atoms in a linear or branched chain;
an alkoxyalkyl, alkylthioalkyl, alkylsulphonylalkyl, monoalkylaminoalkyl, alkenyl or alkynyl radical containing from 2 to 6 carbon atoms in a linear or branched chain;
a dialkylaminoalkyl or cycloalkvl radical containing from 3 to 7 carbon atoms in a linear or branched chain;
an aryl radical, i.e. phenyl, naphthyl, thienyl, furyl, pyridyl, benzothienyl, benzofuryl, cuinolinyl, isoquinolinyl or methylenedioxyphenyl radical, optionally substituted by from 1 to 3 groups selected from $R_6$; and
an arylalkyl, aryloxyalkyl, arylthioalkyl or arylsulphonylalkyl radical, the terms aryl and alkyl having the definitions given above;
or else
$R_1$ and $R_2$, together with the carbon atom to which they are attached on the ring, may form a carbocycle or a heterocycle containing from 5 to 7 atoms, it being possible for these rings to be fused with a phenyl optionally substituted by from 1 to 3 groups selected from $R_6$;
$R_6$ represents a radical selected from:
a halogen atom;
an alkyl, haloalkyl, alkoxy, haloalkoxy, alkylthio, haloalkylthio or alkylsulphonyl radical containing from 1 to 6 carbon atoms;
cycloalkyl, halocycloalkyl, alkenyloxy, alkynyloxy, alkenylthio, alkynylthio radical containing from 3 to 6 carbon atoms;
the nitro or cyano group;
an amino radical optionally mono- or disubstituted by an alkyl or acyl radical containing from 1 to 6 carbon atoms or alkoxycarbonyl radical containing from 2 to 6 carbon atoms; and
a phenyl, phenoxy or pyridyloxy radical, these radicals being optionally substituted by from 1 to 3 identical or different groups selected from $R_7$; and
$R_7$ represents a radical selected from:
a halogen atom selected from fluorine, chlorine, bromine and iodine;
a linear or branched alkyl radical containing from 1 to 6 carbon atoms;
a linear or branched alkoxy or alkylthio radical containing from 1 to 6 carbon atoms;
a linear or branched haloalkoxy or haloalkyithio radical containing from 1 to 6 carbon atoms;
a nitrile radical; and
a nitro radical.

In one preferred embodiment of the invention, the chiral amino acids of formula (I) are such that:
$R_1$ represents an aryl radical optionally substituted by from 1 to 3 groups $R_6$ as defined before, and
$R_2$ represents an alkyl or haloalkyl radical containing from 1 to 6 carbon atoms in a linear or branched chain.

In one very particularly preferred embodiment of the invention, the amino acids of formula (I) are such that:
$R_1$ represents a phenyl radical optionally substituted by a group $R_6$ as defined before, and
$R_2$ represents an alkyl radical selected from methyl, ethyl, linear or branched propyl, linear or branched butyl, linear or branched pentyl and linear or branched hexyl.

Each of the operations (a) to (d) defined above employs techniques which are known to the person skilled in the art who is specialized in organic synthesis. For each of these operations, which are set out in greater detail in the remainder of the description, the person skilled in the art will be able to employ alternatives and/or improvements without departing from the subject-matter of the invention.

The process of the invention allows chiral amino acids to be obtained. By "chiral amino acids" are meant the substantially pure enantiomers either of S configuration or of R configuration.

The term "substantially pure" signifies that the enantiomeric excess of the enantiomer in question is greater than 80%, more particularly greater than 90%. Certain operative conditions of the process of the invention also lead to an enantiomeric excess of 100%; in other words, in this case, the enantiomer obtained is pure, with the other enantiomeric form being undetectable.

By "enantiomeric excess" is meant the ratio of the excess of the desired enantiomer relative to the unwanted enantiomer.

This ratio is calculated in accordance with one of the following equations:

$$\% \ e.e. \ (S) = \frac{[S] - [R]}{[R] + [S]} \times 100$$

$$\% \ e.e. \ (R) = \frac{[R] - [S]}{[R] - [S]} \times 100$$

in which:
% e.e.(S) represents the enantiomeric excess of S isomer,
% e.e.(R) represents the enantiomeric excess of R isomer,
[S] represents the concentration of S isomer, and
[R] represents the concentration of R isomer, The process of the invention is characterized in that an enantiomeric resolving agent and a racemic hydantoin of formula (II)

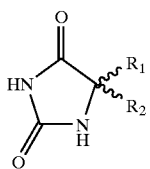
(II)

in which $R_1$ and $R_2$ are as defined before are brought into contact with one another.

By "racemic hydantoin" is meant a substantially optically inactive hydantoin of formula (II), i.e. a hydantoin of formula (II) in which one enantiomer is not present in substantial preponderance over the other.

As preferred base for the process described in the present application, mention may be made of alkali metal hydroxides or alkaline earth metal hydroxides, preferably sodium hydroxide or potassium hydroxide. With very particular preference, the base used is sodium hydroxide. The amount of base used varies between 0.2 and 0.8 equivalents of base relative to the amount of initial racemic hydantoin, preferably between 0.4 and 0.6, for example 0.5 equivalents.

Each of the operations (a) to (d) defined above employs techniques which are known to the person skilled in the art who is specialized in organic synthesis. For each of these operations, which are set out in greater detail in the remainder of the description, the person skilled in the art will be able to employ alternatives and/or improvements without departing from the subject-matter of the invention. Accordingly, such alternatives and/or modifications form an integral part of the present invention.

The totality of the operations (a) to (d) is advantageously carried out in a single step (one-pot reaction); that is to say, without isolation of the that is to say, further, in the same reaction apparatus.

The carrying-out of tne process of the invention in a single step therefore affords a very particular advantage when the process is conducted on the industrial scale.

The first operation of the process of the invention consists in mixing a racemic hydantoin of formula (II) as defined before, a resolving agent and a base with stirring and in a suitably selected solvent. The reaction mixture may optionally be heated in order to allow complete dissolution of the reactants.

The precipitate obtained is separated and mixed with a basic aqueous solution.

The solution thus obtained is treated in order to separate the resolving agent. This separation may be performed by any process known to the person skilled in the art; with particular advantage, this separation is performed by distillation, preferably under reduced pressure. The same procedure is followed for separating the resolving agent present in the filtrate.

In this way, the resolving agent may be separated and recovered in a substantially quantitative fashion and may be reused directly, without other, supplementary treatment, in a new chiral amino acid preparation cycle.

Following removal of the resolving agent, the hydantoin salt solution is subjected to hydrolysis. This operation may advantageously be carried out by simple heating of the reaction mixture.

Finally, the desired chiral amino acid is recovered in accordance with conventional methods, following neutralization of the mixture.

The resolving agent used in the process of the present invention may be any resolving agent known to the person skilled in the art who is specialized in the art of asymmetric synthesis. This resolving agent is of any type suitable for the intended reaction and a chiral (or asymmetric) compound of precise and known configuration, defined generally by the terms dextrorotatory or laevorotatory, which reflect the optical activity of this compound. This resolving agent may be selected, for example, from chiral resolving agents, such as for example chiral amines, such as quinine, cinchonidine, dehydroabiethylamine, ephedrine, 2-amino-1-phenyl-1,3-propanediol, α-methylbenzylamine, α-(1-naphthyl)ethylamine, or 2-phenylglycinol, and chiral acids, such as tartaric acid, dibenzoyltartaric acid, malic acid, camphorsulphonic acid, mandelic acid, or phencyphos. In one very particularly preferred embodiment of the invention, the chiral resolving agent used for the process of the invention is dextrorotatory α-methylbenzylamine, (+)-α-MBA, or laevorotatory α-methylbenzylamine, (−)-α-MBA, depending on whether it methylbenzylamine, (−)-α-MBA, depending on whether It is desired to prepare a dextrorotatory or laevorotatory amino acid, respectively. The use of this resolving agent is described, for example, in the patent WO-A-92/08702 or in the publication by G. Coauerel et al., Chirality, 4, (1992), 400–403.

Surprisingly, the process for preparing chiral amino acids in accordance with the invention may be carried out using not more than one equivalent, for example from 0.2 to 1 equivalent, of resolving agent in relation to the amount of racemic hydantoin, by introducing a base into the reaction mixture during the contacting of the racemic hydantoin with the resolving agent.

This base may be an organic base or an inorganic base. Among the inorganic bases preferred for the process of the invention, mention may be made of hydroxides, for example the hydroxides of alkali metals or alkaline earth metals, for example sodium hydroxide or else potassium hydroxide. As organic base which can be used for the process of the invention, mention may be made of amines, preferably tertiary amines, for example triethylamine.

The base employed for the process of the invention is present in the reaction mixture in an amount of between 0.2 and 0.8 equivalent relative to the amount of racemic hydantoin present at the start.

As preferred base for the process described in the present application, mention may be made of alkali metal hydroxides or alkaline earth metal hydroxides, preferably sodium hydroxide or potassium hydroxide. With very particular preference, the base used is sodium hydroxide. The amount of base used varies between 0.2 and 0.8 equivalents of base relative to the amount of initial racemic hydantoin, preferably between 0.4 and 0.6, for example 0.5 equivalents.

In one embodiment of the process of the present invention, the racemic hydantoin of formula (II) is dissolved. This dissolution is carried out in an organic or inorganic solvent or in a mixture of organic or inorganic solvents or else in a mixture of organic and inorganic solvents. By organic solvent is meant preferably polar protic or aprotic solvents, such as alcohols or ketones, for example methanol, ethanol or dimethyl ketone. By inorganic solvent is meant, again, preferably polar solvents, for example water.

For this purpose the selected ratio of the amounts of water/cosolvent is between 90/10 and 30/70, depending on the nature of the cosolvent.

It is possible, for example, to use a solvent consisting of a mixture of water and ethanol in a 70/30 ratio.

The nature of the solvent for the racemic hydantoin is of particular interest: in effect, a high solvency leads to a high concentration of hydantoin in the reaction mixture, and as a consequence considerably limits the volume of effluence. This last aspect is especially important in the case of an industrial process.

The dissolution of the hydantoin may also be facilitated by heating the reaction mixture. By way of example, the reaction mixture may be heated at temperatures between 40° C. and 80° C., for example between 50° C. and 60° C.

Following dissolution of the racemic hydantoin, addition to the reaction mixture of the resolving agent, and optionally cooling of the whole mixture to a temperature which allows the precipitation of the least-soluble compounds, the precipitate obtained is separated.

An excess of a base in aqueous solution is added to a likewise aqueous solution of this precipitate. The base used is an inorganic base, for example sodium or potassium hydroxide or else ammonium hydroxide. The excess of base added is between 1 and 10 equivalents relative to the amount of initial racemic hydantoin.

Finally, the enantiomeric resolving agent is separated directly from the basic reaction mixture, and may then be reused for the process of the invention. This separation is carried out by any process known to the person skilled in the art. In one very particularly preferred embodiment of the invention, this separation is carried out by distillation.

The reaction mixture then contains a solution of basic chiral hydantoin salt, free of any resolving agent, and this salt is not isolated but is converted directly into the salt of the corresponding chiral amino acid. Here again, this hydrolysis may be carried out by any process known in the literature. For example, hydrolysis is performed by simple heating, at temperatures varying from 50° C. to 250° C., preferably from 100° C. to 200° C., with reaction times varying from several minutes to more than 20 hours, depending on the temperature selected.

Finally, the expected chiral amino acid is isolated from the reaction mixture by the conventional techniques employed in thus field, such as neutralization, washing(s), recrvstallization(s), distrillation(s), drying(s), etc. One or more of these techniques will be able to be performed simultaneously or consecutively under operative conditions which are known to the person skilled in the art, who will know to select the reactants and the reaction conditions which are suitable and appropriate to each case.

The chiral amino acids of formula (I) defined before, obtained by the process of the invention, find especially advantageous application as synthesis intermediates in the preparation of chiral active substances which are useful particularly in therapy or in agriculture.

For example, the chiral amino acids of formula (I) may be used as intermediates in the preparation of certain fungicidal 2-imidazolin-5-ones and 2-imidazoline-5-thiones, described in the patent EP-A-0 629 616, of formula (A):

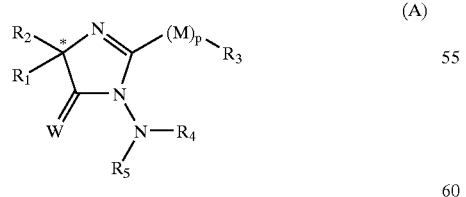

(A)

in which $R_1$ and $R_2$ are as defined before for the amino acids of formula (I) and W represents an oxygen or sulphur atom or an S=O group;
M represents an oxygen or sulphur atom or an optionally halogenated $CH_2$ radical;
is an integer equal to 0 or 1;

$R_3$ represents:
a hydrogen or an optionally halogenated $C_1$–$C_2$ alkyl radical, when p is 0 or $(M)_p$ is a $CH_2$ radical,
an optionally halogenated $C_1$–$C_2$ alkyl radical, when $(M)_p$ represents an oxygen or sulphur atom;

$R_4$ represents:
the hydrogen atom, or
an alkyl radical containing from 1 to 6 carbon atoms, or
an alkoxyalkyl, alkylthioalkyl, haloalkyl, cyanoalkyl, thiocyanatoalkyl, alkenyl or alkynyl radical containing from 2 to 6 carbon atoms, or
a dialkylaminoalkyl, alkoxycarbonylalkyl, or N-alkylcarbamoylalkyl radical containing from 3 to 6 carbon atoms, or
an N,N-dialkylcarbamoylalkyl radical containing from 4 to 8 carbon atoms, or
an aryl radical, comprising phenyl, naphthyl, thienyl, furyl, pyridyl, pyrimidyl, pyridazinyl, pyraz-nyl, benzothienyl, benzofuryl, quinolinyl, isoquinolinyl, or methylenedioxyphenyl, optionally substituted by from 1 to 3 groups selected from $R_6$, or
an arylalkyl, aryloxyalkyl, arylthioalkyl or arylsulphonylalkyl radical, the terms aryl and alkyl having the definitions given above;

$R_5$ represents:
hydrogen, or an alkyl, haloalkyl, alkylsulphonyl, haloalkylsulphonyl radical containing from 1 to 6 carbon atoms or
an alkoxyalkyl, alkylthioalkyl, acyl, alkenyl, alkynyl, haloacyl, alkoxycarbonyl, haloalkoxycarbonyl, alkoxyalkyisulphonyl, cyanoalkylsulphonyl radical containing from 2 to 6 carbon atoms or
an alkoxyalkoxycarbonyl, alkylthioalkoxycarbonyl, cyanoalkoxycarbonyl radical containing from 3 to 6 carbon atoms or
the formyl radical or a cycloalkyl, alkoxyacyl, alkylthioacyl, cyanoacyl, alkenylcarbonyl, alkynylcarbonyl radical containing from 3 to 6 carbon atoms or
a cycloalkylcarbonyl radical containing from 4 to 8 carbon atoms or
a phenyl radical; arylalkylcarbonyl, especially phenylacetyl and phenylpropionyl, arylcarbonyl, especially benzoyl, optionally substituted by from 1 to 3 groups among $R_6$, thienylcarbonyl, furylcarbonyl, pyridylcarbonyl, benzyloxycarbonyl, furfuryloxycarbonyl, tetrahydrofurfuryloxycarbonyl, thienylmethoxycarbonyl, pyridylmethoxycarbonyl, phenoxycarbonyl or phenylthiolcarbonyl, the phenyl radical itself being optionally substituted by from 1 to 3 groups selected rom $R_6$, alky-thiolcarbonyl, haloalkylthiolcarbonyl, alkoxyalkylthiolcarbonyl, cyanoalkylthiolcarbonyl, benzylthiolcarbonyl, furfurylthiolcarbonyl, tetrahydrofurfurylthiolcarbonyl, thienylmethylthiolcarbonyl, pyridylmethylthiolcarbonyl, or arylsulphonyl, or
a carbamoyl radical optionally mono- or disubstituted by:
an alkyl or haloalkyl group containing from 1 to 6 carbon atoms,
a cycloalkyl, alkenyl or alkynyl group containing from 3 to 6 carbon atoms,
an alkoxyalkyl, alkylthioalkyl or cyanoalkyl group containing from 2 to 6 carbon atoms or
a phenyl optionally substituted by from 1 to 3 groups $R_6$;

a sulphamoyl group optionally mono- or disubstituted by:
  an alkyl or haloalkyl group containing from 1 to 6 carbon atoms,
  a cycloalkyl, alkenyl or alkynyl group containing from 3 to 6 carbon atoms,
  an alkoxyalkyl, alkylthioalkyl or cyanoalkyl group of from 2 to 6 carbon atoms or
  a phenyl optionally substituted by from 1 to 3 groups $R_6$;
an alkylthioalkylsulphonyl group containing from 3 to 8 carbon atoms or cycloalkylsulphonyl group containing from 3 to 7 carbon atoms;
$R_4$ and $R_5$ taken together may also form, with the nitrogen atom to which they are attached, a pyrroldino, piperidino, morpholino or piperazino group optionally substituted by an alkyl radical containing from 1 to 3 carbon atoms.

$R^6$ represents:
  a halogen atom or
  an alkyl, haloalkyl, alkoxy, haloalkoxy, alkylthio, haloalkylthio or alkylsulphonyl radical containing from 1 to 6 carbon atoms or
  a cycloalkyl, halocycloalkyl, alkenyloxy, alkynyloxy, alkenylthio, alkynylthio radical containing from 3 to 6 carbon atoms or
  the nitro or cyano group or
  an amino radical optionally mono- or disubstituted by an alkyl or acyl radical containing from 1 to 6 carbon atoms or alkoxycarbonyl radical containing from 2 to 6 carbon atoms,
  a phenyl, phenoxy or pyridyloxy radical, these radicals being optionally substItuted by from 1 to 3 ident-cal or different groups selected from $R_7$, $R_7$ represents:
  a halogen atom selected from fluorine, chlorine, bromne, iodine or
  an alkyl radical containing from 1 to 6 carbon atoms, or
  an alkoxy or alkylthio radical containing from 1 to 6 carbon atoms or
  a haloalkoxy or haloalkylthio radical containing from 1 to 6 carbon atoms or
  a nitrile or nitro radical;

The process for preparing compounds of

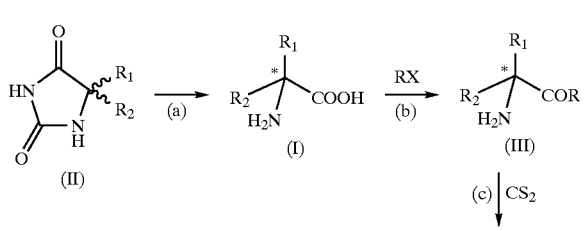

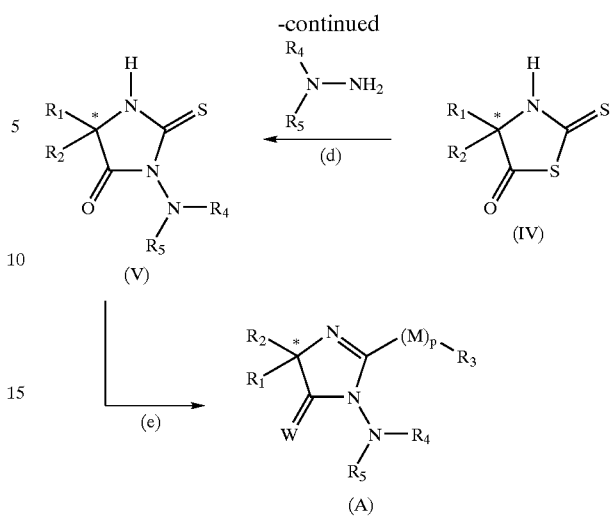

in which scheme the radicals $R_1$, $R_2$, $R_3$, $R_4$, $R_5$, M, p and W are as defined before, R represents a hydroxyl radical, an alkoxy radical containing from 1 to 6 carbon atoms, or a benzyloxy radical, an amino, alkylamino or dialkylamino radical, or an alkylamino radical containing from 1 to 6 carbon atoms, and X represents a leaving group such as a halogen atom, selected from chlorine, bromine and iodine, or a sulphate radical, or alkylsulphonyloxy or arylsulphonyloxy.

In the above scheme
  step (a) is the process of the present invention and is exemplified in the remainder of the present description;
  steps (b), (c) and (d) are described in the patent WO-98/03490, whose detail is incorporated here by reference;
  step (e) is described in the patent EP-A-0 629 616, whose detail is incorporated here by reference.

The overall process for synthesis of compounds of formula (A) from racemic hydantoins of formula (II) via the. intermediates of formula (I) is novel and is therefore included within the scope of the present invention.

The following examples will permit the subject-matter and advantages of the process of the invention to be illustrated and better appreciated, but without limiting the scope of the said invention.

EXAMPLE 1

In a solvent consisting of water and ethanol in a 70/30 ratio, and with stirring, 15.7 mmoles of racemic 5-methyl-5-phenylhydantoin, 15.7 mmoles of R-(+)-α-methylbenzylamine and 7.85 mmoles of sodium hydroxide are mixed.

The reaction mixture is heated at 50° C. for 1.5 h and then cooled to 10° C.

The precipitate is filtered off and then washed with water.

This precipitate is subsequently dissolved in water in the presence of sodium hydroxide (0.3 equivalent by weight of precipitate). The solution obtained is subjected to an azeotropic distillation under reduced pressure (400 mbar) for quantitative recovery of R-(+)-α-methylbenzylamine.

The reaction medium is then heated at 140° C. for 4 h.

After it has been cooled to 25° C., the reaction mixture is acidified with 33% aqueous hydrochloric acid.

The precipitate of chiral amino acid obtained is then filtered off and subsequently washed (water, acetone) and dried under vacuum.

This gives the expected dextrorotatory chiral amino acid with a yield of 32% relative to the initial racemic hydantoin and an enantiomeric excess of 97%.

EXAMPLE 2

In a solvent consisting of water and methanol in a 70/30 ratio, and with stirring, racemic 5-methyl-5-phenylhydantoin, R-(+)-α-methylbenzylamine (0.9 equivalent relative to the amount of racemic 5-methyl-5-phenylhydantoin) and sodium hydroxide (0.5 equivalent relative to the amount of racemic 5-methyl-5-phenylhydantoln) are mixed.

The reaction mixture is heated at 55° C. for 30 min and then cooled to 20° C.

The mixture is filtered and then the precipitate obtained is washed with water.

This precipitate is subsequently dissolved in water in the presence of sodium hydroxide (0.3 equivalent by weight of precipitate), and R-(+)-α-methylbenzylamine is separated by distillation from the solution obtained.

The reaction medium is then heated at 160° C. for 4 h.

After it has been cooled to 25° C., the reaction mixture is acidified with 33% aqueous hydrochloric acid.

The precipitate of chiral amino acid obtained is then filtered off, which is then washed and, finally, dried.

This gives S-(+)-methylphenylglycine with a yield of 33% relative to the initial racemic hydantoin and an enantiomeric excess of 98%.

What is claimed is:

1. Process for preparing chiral amino acids of formula (I):

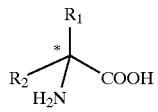

(I)

in which:

$R_1$ and $R_2$ are different and are selected from:
an alkyl or haloalkyl radical containing from 1 to 6 carbon atoms in a linear or branched chain;
an alkoxyalkyl, alkylthioalkyl, alkylsulphonylalkyl, monoalkylaminoalkyl, alkenyl or alkynyl radical containing from 2 to 6 carbon atoms in a linear or branched chain;
a dialkylaminoalkyl or cycloalkyl radical containing from 3 to 7 carbon atoms in a linear or branched chain;
an aryl radical, optionally substituted by from 1 to 3 individually selected $R_6$ groups; and
an arylalkyl, aryloxyalkyl, arylthioalkyl or arylsulphonylalkyl radical;
or else $R_1$ and $R_2$, together with the carbon atom to which they are attached on the ring, form a carbocycle or a heterocycle containing from 5 to 7 atoms, including these rings being fused with a phenyl optionally substituted by from 1 to 3 individually selected $R_6$ groups;

$R_6$ represents a radical selected from:
a halogen atom;
an alkyl, haloalkyl, alkoxy, haloalkoxy, alkylthio, haloalkylthio or alkylsulphonyl radical containing from 1 to 6 carbon atoms;
a cycloalkyl, halocycloalkyl, alkenyloxy, alkynyloxy, alkenylthio, alkynylthio radical containing from 3 to 6 carbon atoms;
a nitro or cyano group;
an amino radical optionally mono- or disubstituted by an alkyl or acyl radical containing from 1 to 6 carbon atoms or alkoxycarbonyl radical containing from 2 to 6 carbon atoms; and
a phenyl, phenoxy or pyridyloxy radical, these radicals being optionally substituted by from 1 to 3 identical or different $R_7$ groups; and $R_7$ represents a radical selected from:
a fluorine, chlorine, bromine or iodine atom;
a linear or branched alkyl radical containing from 1 to 6 carbon atoms;
a linear or branched alkoxy or alkylthio radical containing from 1 to 6 carbon atoms;
a linear or branched haloalkoxy or haloalkylthio radical containing from 1 to 6 carbon atoms;
a nitrile radical; and
a nitro radical, said process comprising the steps of:

(A) dissolving a racemic hydantoin of formula (II):

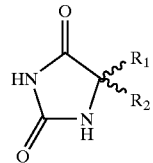

(II)

in a basic medium used in an amount of from 0.2 to 0.8 equivalent of base relative to the amount of said racemic hydantoin;

(B) adding an enantiomeric resolving agent in an amount of from 0.2 to 1.0 equivalent of resolving agent relative to the amount of said racemic hydantoin;

(C) separating the resolving agent from the reaction mixture; and (D) hydrolysing the reaction mixture in a basic medium in order to liberate the basic salt of the desired chiral amino acid, which process is conducted in a water/cosolvent mixture.

2. Process according to claim 1, characterized in that it is carried out in a one pot reaction.

3. Process according to claim 2, characterized in that the resolving agent is a chiral amine or a chiral acid.

4. Process according to claim 3, characterized in that the resolving agent is R-(+)-α-methylbenzylamine or S-(-)-α-methylbenzylamine.

5. Preparation process according to claim 1, characterized in that it is carried out using from 0.4 to 0.6 equivalents of an organic or inorganic base relative to the amount of racemic hydantoin employed.

6. Process according to claim 1, characterized in that the cosolvent is methanol, ethanol or acetone.

7. Process according to claim 1, characterized in that the water/cosolvent ratio is such the concentration of racemic hydantoin is between 5 and 30% by weight in the reaction mixture.

8. Process according to claim 7, characterized in that the water/cosolvent ratio is between 90/10 and 30/70.

9. Process according to claim 1, characterized in that the resolving agent is separated after reaction and recovered in substantially quantitative fashion in order to be reused directly, without other, supplementary treatment, in a new chiral amino acid preparation cycle.

10. Process according to claim 1, characterized in that:
  $R_1$ represents an aryl radical optionally substituted by from 1 to 3 individually selected $R_6$ groups; and
  $R_2$ represents an alkyl or haloalkyl radical containing from 1 to 6 carbon atoms in a linear or branched chain.

11. Process according to claim 10, characterized in that:
  $R_1$ represents a phenyl radical optionally substituted by a $R_6$ group; and
  $R_2$ represents an alkyl radical selected from the group consisting of methyl, ethyl, linear or branched propyl, linear or branched butyl, linear or branched pentyl and linear or branched hexyl.

12. Process according to claim 1, characterized in that it is carried out using from 0.2 to 1 equivalent of resolving agent in relation to the amount of racemic hydantoin employed.

13. Process according to claim 1, characterized in that the resolving agent is a chiral amine or a chiral acid.

14. Process according to claim 13, characterized in that the resolving agent is R-(+)-α-methylbenzylamine or S-(−)-α-methylbenzylamine.

15. Process according to claim 1, further characterized in that the racemic hydantoin is converted into the chiral amino acid of formula (I) and thereafter to a compound of formula (A) by the reaction sequence:

in which:
  W represents an oxygen or sulphur atom or an S=O group;
  M represents an oxygen or sulphur atom or an optionally halogenated $CH_2$ radical;
  p is an integer equal to 0 or 1;
  $R_3$ represents:
    a hydrogen or an optionally halogenated $C_1$–$C_2$ alkyl radical, when p is 0 or $(M)_p$ is a $CH_2$ radical, or
    an optionally halogenated $C_1$–$C_2$ alkyl radical, when $(M)_p$ represents an oxygen or sulphur atom;
  $R_4$ represents:
    a hydrogen atom, or
    an alkyl radical containing from 1 to 6 carbon atoms, or
    an alkoxyalkyl, alkylthioalkyl, haloalkyl, cyanoalkyl, thiocyanatoalkyl, alkenyl or alkynyl radical containing from 2 to 6 carbon atoms, or
    a dialkylaminoalkyl; alkoxycarbonylalkyl, or N-alkylcarbamoylalkyl radical containing from 3 to 6 carbon atoms, or
    an N,N-dialkylcarbamoylalkyl radical containing from 4 to 8 carbon atoms, or
    an aryl radical, optionally substituted by from 1 to 3 individually selected $R_6$ groups, or
    an arylalkyl, aryloxyalkyl, arylthioalkyl or arylsulphonylalkyl radical;
  $R_5$ represents:
    hydrogen, or an alkyl, haloalkyl, alkylsulphonyl, haloalkylsulphonyl radical containing from 1 to 6 carbon atoms or
    an alkoxyalkyl, alkylthioalkyl, acyl, alkenyl, alkynyl, haloacyl, alkoxycarbonyl, haloalkoxycarbonyl, alkoxyalkylsulphonyl, cyanoalkylsulphonyl radical containing from 2 to 6 carbon atoms or
    an alkoxyalkoxycarbonyl, alkylthioalkoxycarbonyl, cyanoalkoxycarbonyl radical containing from 3 to 6 carbon atoms or
    the formyl radical or a cycloalkyl, alkoxyacyl, alkylthioacyl, cyanoacyl, alkenylcarbonyl, alkynylcarbonyl radical containing from 3 to 6 carbon atoms or
    a cycloalkylcarbonyl radical containing from 4 to 8 carbon atoms or
    a phenyl radical; arylalkylcarbonyl, arylcarbonyl, optionally substituted by from 1 to 3 individually selected $R_6$ groups, thienylcarbonyl, furylcarbonyl, pyridylcarbonyl, benzyloxycarbonyl, furfuryloxycarbonyl, tetrahydrofurfuryloxycarbonyl, thienylmethoxycarbonyl, pyridylmethoxycarbonyl, phenoxycarbonyl or phenylthiolcarbonyl, the phenyl radical itself being optionally substituted by from 1 to 3 individually selected $R_6$ groups, alkylthiolcarbonyl, haloalkylthiolcarbonyl, alkoxyalkylthiolcarbonyl, cyanoalkylthiolcarbonyl, benzylthiolcarbonyl, furfurylthiolcarbonyl, tetrahydrofurfurylthiolcarbonyl, thienylmethylthiolcarbonyl, pyridylmethylthiolcarbonyl, or arylsulphonyl, or
    a carbamoyl radical optionally mono- or disubstituted by:
      an alkyl or haloalkyl group containing from 1 to 6 carbon atoms,
      a cycloalkyl, alkenyl or alkynyl group containing from 3 to 6 carbon atoms,
      an alkoxyalkyl, alkylthioalkyl or cyanoalkyl group containing from 2 to 6 carbon atoms or
      a phenyl optionally substituted by from 1 to 3 groups $R_6$;
    a sulphamoyl group optionally mono- or disubstituted by:
      an alkyl or haloalkyl group containing from 1 to 6 carbon atoms,
      a cycloalkyl, alkenyl or alkynyl group containing from 3 to 6 carbon atoms,
      an alkoxyalkyl, alkylthioalkyl or cyanoalkyl group of from 2 to 6 carbon atoms or
      a phenyl optionally substituted by from 1 to 3 individually selected $R_6$ groups;

an alkylthioalkylsulphonyl group containing from 3 to 8 carbon atoms or cycloalkylsulphonyl group containing from 3 to 7 carbon atoms;

or else $R_4$ and $R_5$ taken together may also form, with the nitrogen atom to which they are attached, a pyrrolidino, piperidino, morpholino or piperazino group optionally substituted by an alkyl radical containing from 1 to 3 carbon atoms;

R represents a hydroxyl radical, an alkoxy radical containing from 1 to 6 carbon atoms, or a benzyloxy radical, an amino, alkylamino or dialkylamino radical, or an alkylamino radical containing from 1 to 6 carbon atoms, and X represents a leaving group.

16. Process according to claim 15, characterized in that X represents chlorine, bromine, iodine, sulphate, alkylsulphonyloxy or arylsulphonyloxy.

* * * * *